(12) United States Patent
Kim et al.

(10) Patent No.: US 8,564,397 B2
(45) Date of Patent: Oct. 22, 2013

(54) STRUCTURE AND METHOD FOR ATTACHING TACTILE SENSOR TO CURVED SURFACE

(75) Inventors: Jong Ho Kim, Daejeon (KR); Min Seok Kim, Daejeon (KR); Yon-Kyu Park, Daejeon (KR); Dae Im Kang, Daejeon (KR); Dong-Ki Kim, Gwangju-si (KR)

(73) Assignee: Korea Research Institute of Standards and Science, Daejeon (KR)

( * ) Notice: Subject to any disclaimer, the term of this patent is extended or adjusted under 35 U.S.C. 154(b) by 1 day.

(21) Appl. No.: 13/421,945

(22) Filed: Mar. 16, 2012

(65) Prior Publication Data

US 2013/0168336 A1 Jul. 4, 2013

(30) Foreign Application Priority Data

Dec. 28, 2011 (KR) .......................... 10-2011-0144614

(51) Int. Cl.
*H01C 10/10* (2006.01)

(52) U.S. Cl.
USPC .............................. 338/47; 338/114; 338/210

(58) Field of Classification Search
USPC .................... 338/47, 114, 210, 211
See application file for complete search history.

(56) References Cited

U.S. PATENT DOCUMENTS

| | | | | |
|---|---|---|---|---|
| 6,479,890 B1 * | 11/2002 | Trieu et al. | .................... | 257/678 |
| 6,886,415 B1 * | 5/2005 | Kurogi et al. | ............ | 73/862.045 |
| 7,768,376 B2 * | 8/2010 | Liu et al. | ..................... | 338/22 R |
| 7,878,075 B2 * | 2/2011 | Johansson et al. | ....... | 73/862.046 |
| 2006/0254369 A1 * | 11/2006 | Yoon et al. | ............... | 73/862.041 |
| 2011/0253626 A1 * | 10/2011 | Everett | .......................... | 210/631 |

OTHER PUBLICATIONS

Someya et al., "Conformable, flexible, large-area networks of pressure and thermal sensors with organic transistor active matrixes," Proc. National Academy of Sciences of USA, vol. 102, No. 35, pp. 12321-12325, Aug. 30, 2005.

* cited by examiner

*Primary Examiner* — Kyung Lee

(74) *Attorney, Agent, or Firm* — Allen, Dyer, Doppelt, Milbrath & Gilchrist, P.A.

(57) ABSTRACT

The present invention relates to a structure for attaching tactile sensors to a curved surface, comprising a sensor fixing unit configured to have at least part of one surface curved and to have a plurality of sensor insertion grooves, crossing each other, formed in the one surface in a matrix form; tactile sensor units formed in a matrix form, inserted into the respective sensor insertion grooves, and configured to detect external force; sealing units configured to seal the respective sensor insertion grooves; and a support unit configured to come in contact with one face of the sealing units or the sensor fixing units and to support the sensor fixing units. Accordingly, the tactile sensors can be easily attached to a curved surface, and mass production is possible.

16 Claims, 11 Drawing Sheets

STRUCTURE AND METHOD FOR ATTACHING TACTILE SENSOR TO CURVED SURFACE

CROSS-REFERENCE TO RELATED APPLICATION

Priority to Korean patent application number 10-2011-0144614 filed on Dec. 28, 2011, the entire disclosure of which is incorporated by reference herein, is claimed.

BACKGROUND OF THE INVENTION

1. Field of the Invention

The present invention relates to a structure and method for attaching tactile sensors to a curved surface and, more particularly, to a structure and method for attaching a curved surface type tactile sensor, wherein the tactile sensor is inserted into a sensor fixing unit having sensor insertion grooves formed in a concave or convex curved surface, thereby enabling the tactile sensor to be easily attached to the curved surface and enabling mass production.

2. Background of the Related Art

A tactile function for obtaining pieces of information (i.e., the intensity of contact force, vibration, surface roughness, and a temperature change of thermal conductivity) about surrounding environments through a contact is being understood as the next-generation information gathering medium. A bio-mimetic tactile sensor replaceable with a tactile sense becomes more important because it may be used in a variety of medical diagnoses and operations, such as a micro operation within a blood vessel and a cancer diagnosis and applied to tactile sensation proposal technology important in the future virtual environment implementation technology.

The bio-mimetic tactile sensor is for a force/torque sensor of 6 degrees of freedom which is already used in the wrist of an industrial robot and the gripper of a robot and is configured to detect contact pressure and instant sliding, but is problematic in that it has a low sensitivity owing to a relatively bulky detection unit.

FIG. 1 is a conceptual diagram of an artificial skin attached to a two-dimensional curved surface, and FIG. 2 is a conceptual diagram of an artificial skin attached to a three-dimensional curved surface. In order to give a tactile sensation to a machine, artificial skins 11 and 21 may be implemented by attaching a bio-mimetic tactile sensor. The conventional tactile sensor is formed of a flat film and may be attached to an object 10 having a two-dimensional curved surface, such as that shown in FIG. 1, but may not be attached to an object 20 having a three-dimensional curved surface, such as that shown in FIG. 2. Accordingly, there is a need for a flexible tactile sensor.

There is a possibility that the tactile sensor may be developed using Micro-ElectroMechanical Systems (MEMS) technology. However, this technology is problematic in that the tactile sensor does not have flexibility because a sensor is formed using a silicon wafer.

FIG. 3 is an explanatory diagram showing an example of a conventional tactile sensor. The conventional tactile sensor of FIG. 3 was made public by a Takao Someya group in the University of Tokyo in 2005. In accordance with this technology, a tactile sensor 31 was formed of a single film through a punching process, thereby partially implementing flexibility and extensibility. Accordingly, the tactile sensor 31 can also be attached to a globular shape 30. The tactile sensor 31 fabricated by the punching process, however, does not have the greatest flexibility because a sheet of a film is punched in order to give flexibility. Accordingly, the tactile sensor 31 may be applied to a globular shape having a large cylinder or a large curvature, but has a problem in that it may not be applied to an organ, such as a finger of a human type robot, or a very small globular shape because it lacks soft like a human skin. Furthermore, there are problems in that automation is difficult and an individual manual work is necessary because the tactile sensor 31 must be attached one by one.

FIG. 4 is a perspective view showing another example of a conventional tactile sensor. The conventional tactile sensor of FIG. 4 was made public by a Wagner group of Princeton University in 2005. A tactile sensor 41 according to this technology includes metal lines 41b formed on a polydimethylsiloxane (PDMS) substrate 41a and a fixing cell 41c formed at a crossing of the metal lines 41b. The tactile sensor 41, however, is problematic in that a crack is generated in the metal line 41b if peeling is generated between the metal lines 41b and the substrate 41a or if slight deformation occurs and the tactile sensor 41 is worn by a continuous contact.

Someya, T., Kato, Y., Sekitani, T., Iba, S., Noguchi, Y., Murase, Y., Kawaguchi, H. and Sakurai, T., "Conformable, flexible, large-area networks of pressure and thermal sensors with organic transistor active matrixes," Proc. National Academy of Sciences of USA, Vol. 102, No. 35, pp. 12321-12325, 2005.

SUMMARY OF THE INVENTION

Accordingly, the present invention has been made in view of the above problems occurring in the prior art, and it is an object of the present invention to provide a structure and method for attaching a curved surface type tactile sensor, wherein the tactile sensor is inserted into a sensor fixing unit having sensor insertion grooves formed in a concave or convex curved surface, thereby enabling the tactile sensor to be easily attached to the curved surface and enabling mass production.

Further objects, specific merits and novel characteristics of the invention will become more apparent from the following detailed description and exemplary embodiments taken in conjunction with the accompanying drawings.

The above object of the present invention may be achieved by a structure for attaching tactile sensors to a curved surface, comprising a sensor fixing unit configured to have at least part of one surface curved and to have a plurality of sensor insertion grooves, crossing each other, formed in the one surface in a matrix form; tactile sensor units formed in a matrix form, inserted into the respective sensor insertion grooves, and configured to detect external force; sealing units configured to seal the sensor insertion grooves; and a support unit configured to come in contact with one face of the sealing units or the sensor fixing units and to support the sensor fixing units.

Furthermore, the tactile sensor unit detects the external force by using any one of a contact resistance method, a capacitive method, a piezoelectric material method, and a pressure resistance method.

Furthermore, each of the tactile sensor units comprises a first sensor layer configured to include a plurality of first sensing units wired in one direction and inserted into respective crossings of the sensor insertion grooves and a second sensor layer configured to include a plurality of second sensing units, wired in one direction and inserted into respective crossings of the sensor insertion grooves, and stacked to cross the first sensor layer.

The structure further comprises load bumpers provided between the tactile sensor unit and the sensor fixing unit.

The structure further comprises a locking unit coupled with one side of at least one of the sensor fixing unit and the sealing unit and configured to couple the sensor fixing unit and the support unit.

Furthermore, at least one of the sensor fixing unit and the sealing unit further comprises grooves/protrusions formed one side, and the locking unit comprises locking protrusions/locking grooves coupled with the grooves/protrusions.

Furthermore, the sensor fixing unit comprises sensor fixing protrusions formed on one side, and fixing grooves formed to be coupled with the sensor fixing protrusions are formed in respective parts into which the sensor insertion grooves are not inserted, from the tactile sensor unit.

Furthermore, the locking unit is combined with one side of the sensor fixing unit by using bonding.

Furthermore, the tactile sensor unit is combined with one side of the sensor fixing unit by using bonding.

Furthermore, the sensor fixing unit has the one surface in which the sensor insertion grooves are formed concavely curved.

The structure further comprises a temperature sensor unit provided between the tactile sensor and the sensor fixing unit and configured to detect temperature.

Furthermore, the sensor fixing unit has the one surface in which the sensor insertion grooves are formed convexly curved.

The structure further comprises a temperature sensor unit provided between the tactile sensor unit and the sealing unit and configured to detect temperature.

Furthermore, the sealing unit is curved to have an identical curvature with the sensor fixing unit.

Furthermore, the depth of the sensor insertion groove is 0.5 times to 3 times the thickness of the sealing unit.

Furthermore, at least one of the sensor fixing unit and the sealing unit comprises at least one of flexible polyurethane, PDMS, silicon, latex, and synthetic resin materials.

Meanwhile, the above object of the present invention is achieved by a method of attaching tactile sensors to a curved surface, comprising the steps of inserting at least part of tactile sensor units into sensor insertion grooves of a matrix form which are formed in a curved surface of a sensor fixing unit and sealing a plurality of sensor insertion grooves with respective sealing units.

The method further comprises the step of coupling the locking unit and one side of the sensor fixing unit, after the sealing step.

The method further comprises the step of inserting a support unit between the sensor fixing unit and the locking unit, after the step of coupling the locking unit.

Furthermore, grooves/protrusions are formed on one side of at least one of the sensor fixing unit and the sealing unit, locking protrusions/locking grooves coupled with the grooves/protrusions are formed in the locking unit, and the locking protrusion/locking grooves are combined with the grooves/protrusions.

Furthermore, the step of coupling the locking unit includes combining the locking unit with one side of the sensor fixing unit by using bonding.

Furthermore, sensor fixing protrusions are formed in one side of the sensor fixing unit, fixing grooves are formed at edges of the tactile sensor unit, and the step of inserting the tactile sensor unit or the sealing step includes the step of combining the fixing grooves of the tactile sensor unit with the sensor fixing protrusions.

The method as claimed in claim 17, wherein the step of inserting the tactile sensor unit or the sealing step includes the step of bonding and fixing at least part of the tactile sensor unit to one side of the sensor fixing unit.

Furthermore, the step of insetting the tactile sensor unit comprises the steps of inserting a second sensor layer, comprising a plurality of second sensing units wired in one direction, into the sensor insertion groove and stacking a first sensor layer comprising a plurality of first sensing units wired in one direction so that the first sensor layer crosses the second sensor layer and inserting the first sensor layer into the sensor insertion groove.

Furthermore, a load bumper is stacked and formed on one face of the second sensing unit, and the second sensor layer is inserted so that the load bumper is directed toward the crossing of the sensor insertion grooves.

Furthermore, a surface in which the sensor insertion grooves are formed is concavely curved.

The method further comprises the step of inserting the temperature sensor unit into the sensor insertion groove, before the step of inserting the tactile sensor unit.

Furthermore, a surface in which the sensor insertion grooves are formed is convexly curved.

The method further comprises the step of inserting the temperature sensor unit into the sensor insertion groove, after the step of inserting the tactile sensor unit.

Furthermore, the sealing step includes the sensor fixing unit and the sealing unit.

BRIEF DESCRIPTION OF THE DRAWINGS

The following drawings attached to this specification illustrate preferred embodiments of the present invention and function to further assist understanding of the technical spirit of the present invention together with the detailed description of the present invention. Therefore, the present invention should not be construed as being limited to only matters written in the drawings.

DESCRIPTION OF REFERENCE NUMERALS OF PRINCIPAL ELEMENTS IN THE DRAWINGS

Figure 1:
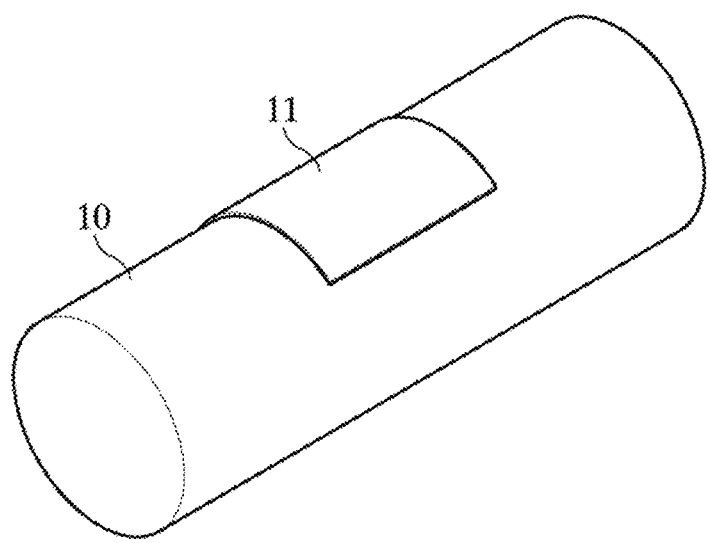
FIG. 1 is a conceptual diagram of an artificial skin attached to a two-dimensional curved surface.
Figure 2:
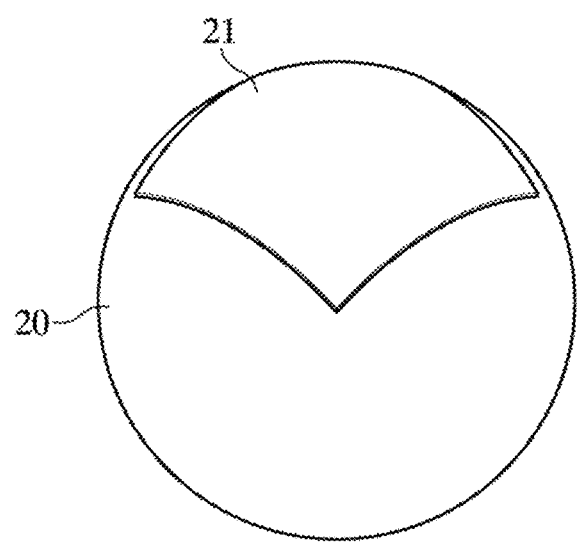
FIG. 2 is a conceptual diagram of an artificial skin attached to a three-dimensional curved surface.
Figure 3:
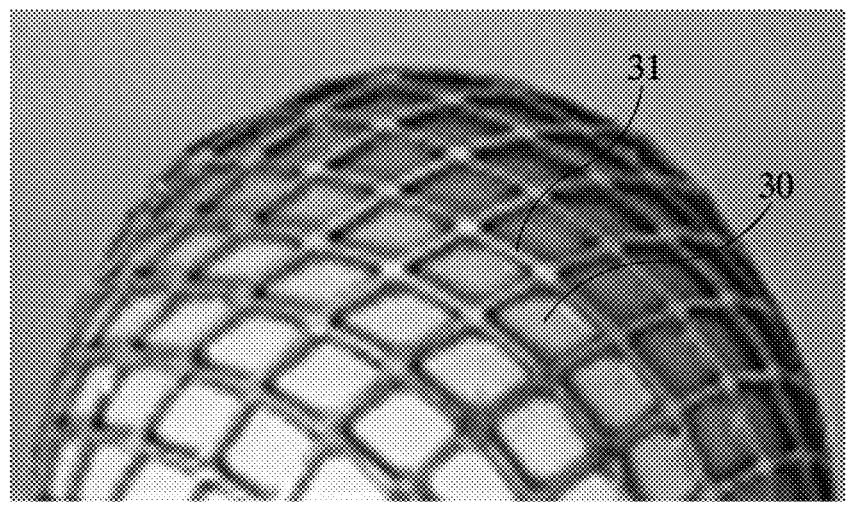
FIG. 3 is an explanatory diagram showing an example of a conventional tactile sensor.
Figure 4:
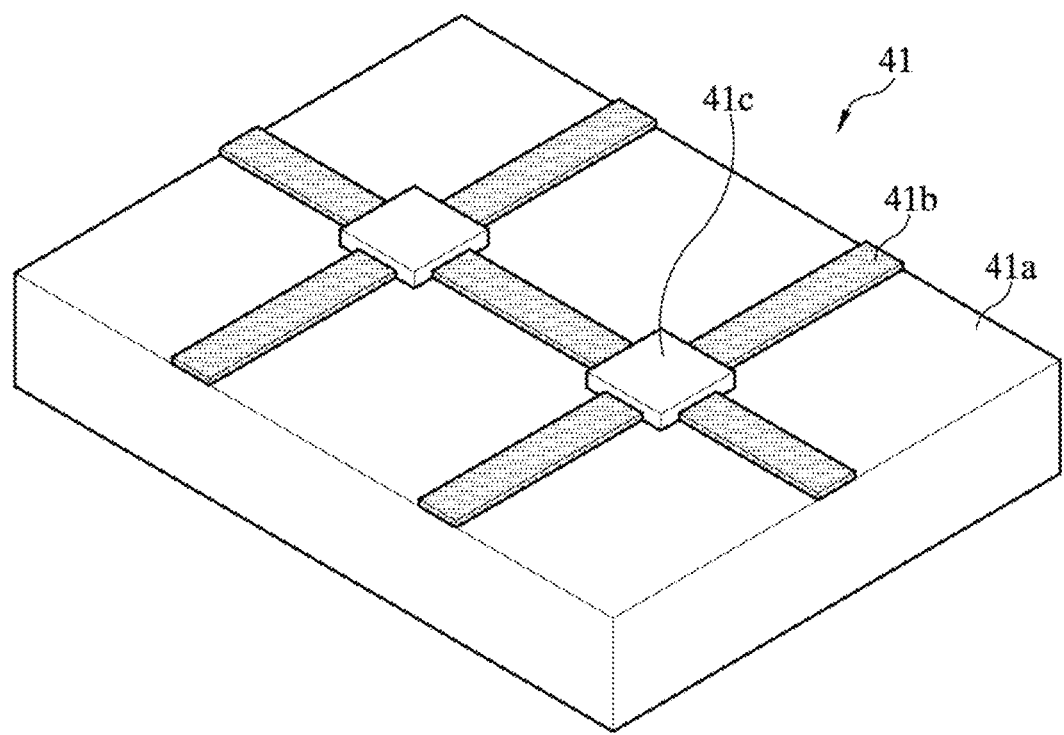
FIG. 4 is a perspective view showing another example of a conventional tactile sensor.

| | |
|---|---|
| 10: object having two-dimensional curved surface | |
| 11, 21: artificial skin | |
| 20: object having three-dimensional curved surface | |
| 30: globular shape | |
| 31, 41: conventional tactile sensor | 41a: PDMS |
| 41b: metal line | 41c: fixing cell |
| 100: tactile sensor unit | 110: first sensor layer |
| 111: first sensing unit | 112: first signal line |
| 113: fixing groove | 120: second sensor layer |
| 121: second sensing unit | 122: second signal line |
| 130: load bumper | 140: temperature sensor unit |
| 200: sensor fixing unit | 210: sensor insertion groove |
| 220: protrusion | 300: sealing unit |
| 400: support unit | 500: locking unit |
| 510: locking groove | Rc: feedback resistor |
| Rs: resistor of contact resistance sensor | |
| Rt: temperature compensation resistor having PTC characteristic or NTC characteristic | |

DETAILED DESCRIPTION OF EMBODIMENTS

Hereinafter, preferred embodiments of the present invention are described in detail with reference to the accompanying drawings in order for those skilled in the art to be able to readily practice them. In describing the operational principle relating to the preferred embodiments of the present invention, when a detailed description of relevant functions or constructions is determined to make unnecessarily obscure the subject matter of the present invention, the detailed description will be omitted.

Construction of First Embodiment

A structure for attaching tactile sensors to a curved surface according to a first embodiment of the present invention chiefly includes tactile sensor units 100, load bumpers 130, temperature sensor units 140, a sensor fixing unit 200, sealing units 300, a support unit 400, and a locking unit 500.

Figure 5:
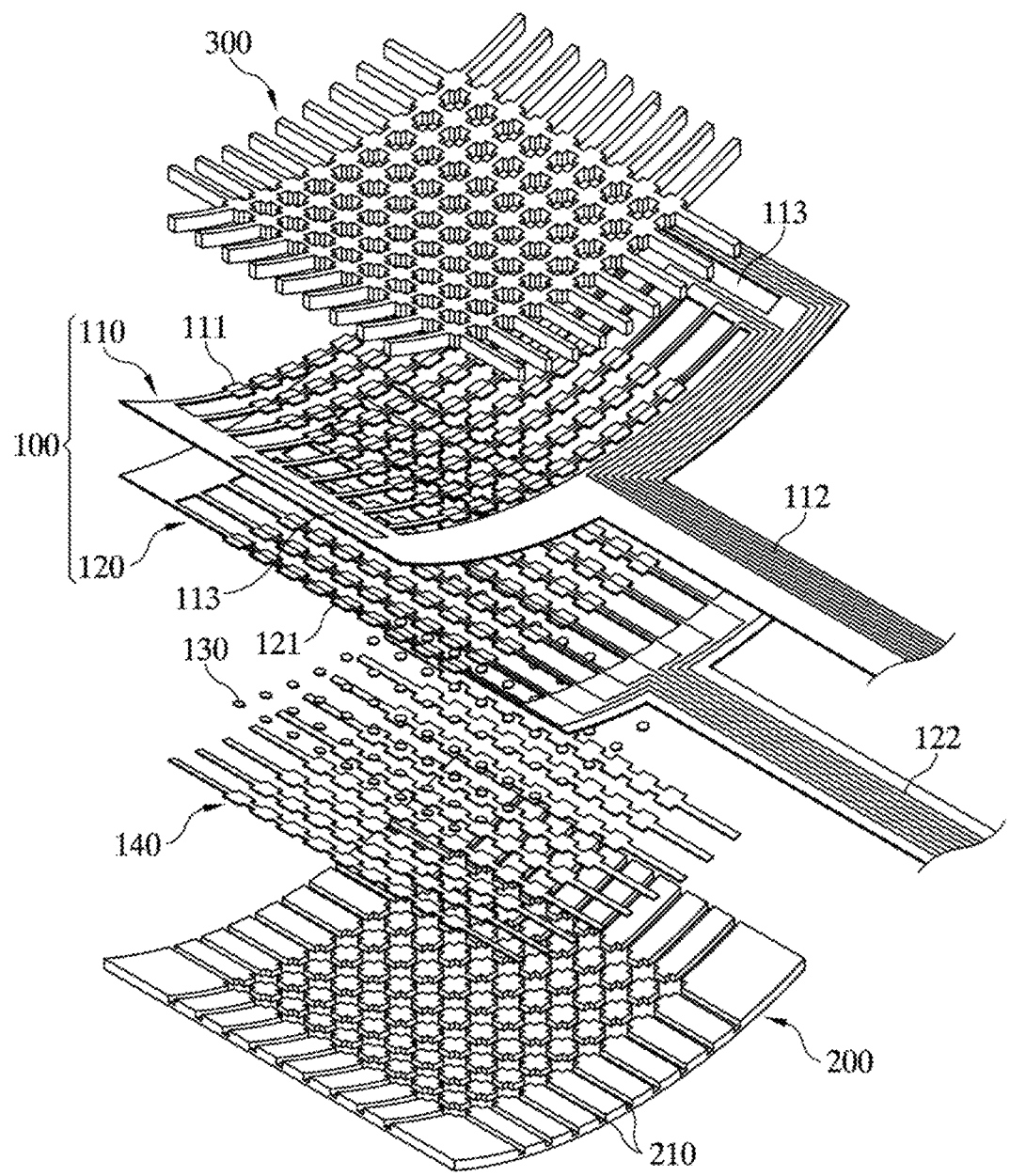
FIG. 5 is an exploded perspective view of a tactile sensor unit to a sealing unit, from among elements forming a structure for attaching tactile sensors to a curved surface according to a first embodiment of the present invention.
Figure 6:
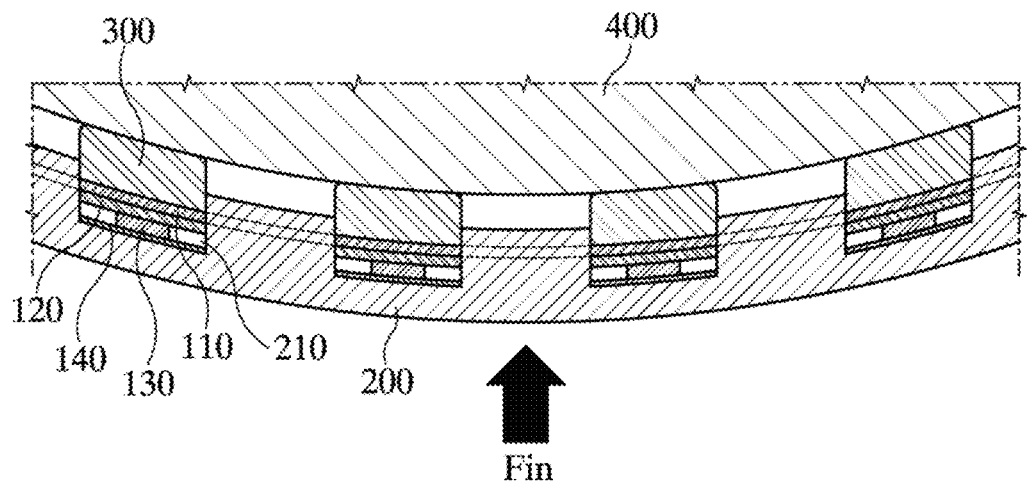
FIG. 6 is a partial sectional view of the structure for attaching tactile sensors to a curved surface according to the first embodiment of the present invention.
Figure 7:
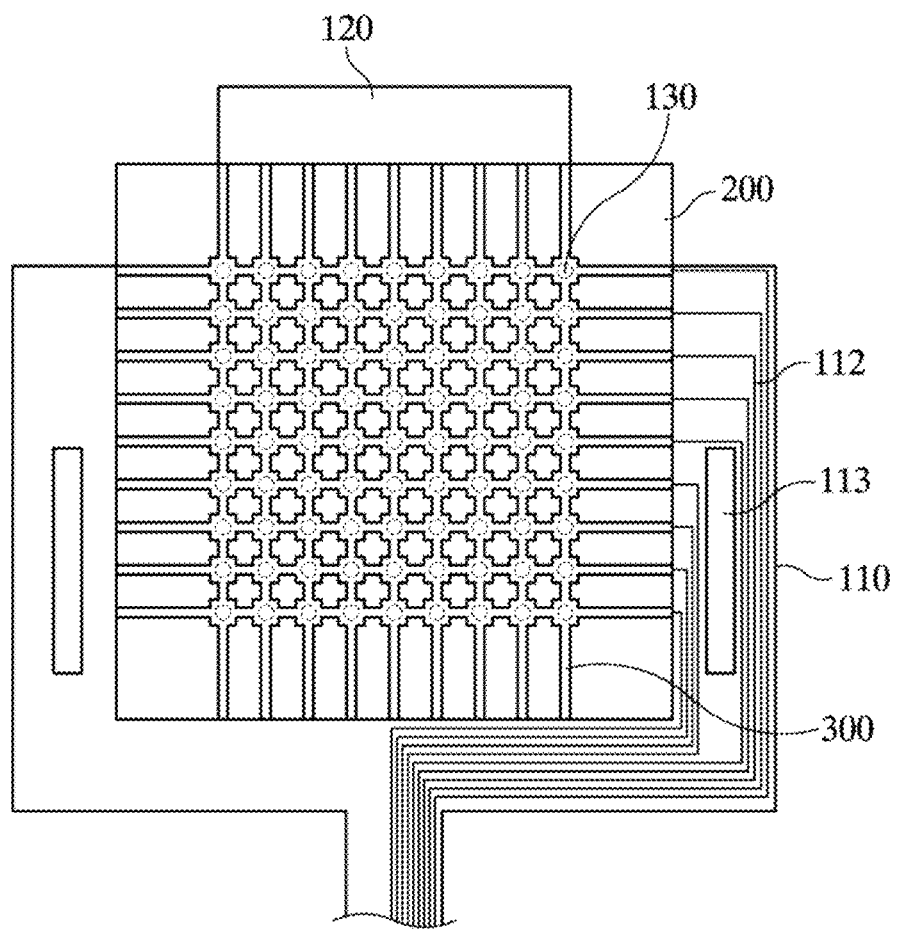
FIG. 7 is a plan view of FIG. 5.
Figure 8:
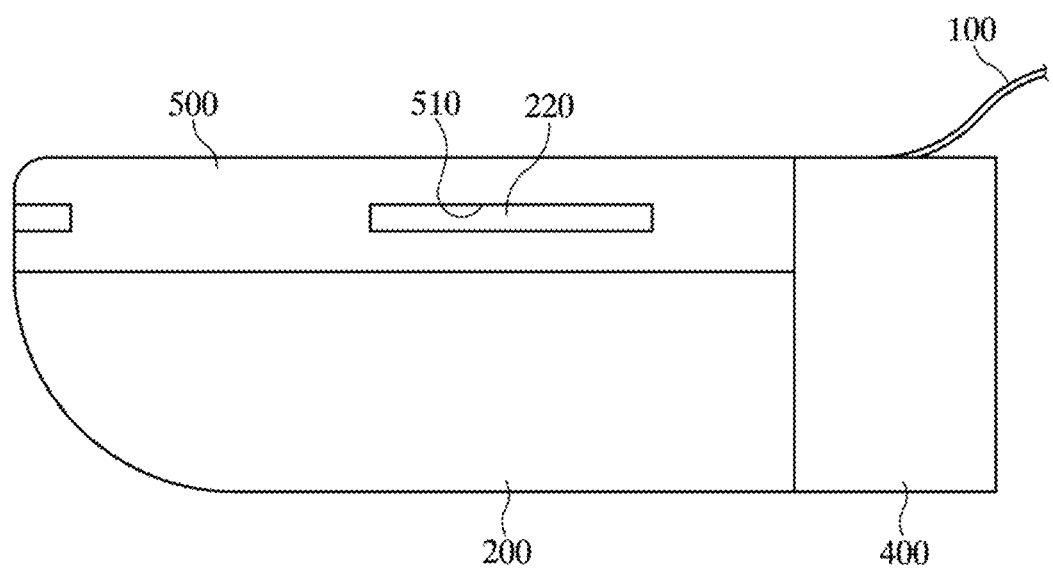
FIG. 8 is a side view of the structure for attaching tactile sensors to a curved surface according to the first embodiment of the present invention.

FIG. 5 is an exploded perspective view of the tactile sensor unit to the sealing unit, from among the elements forming the structure for attaching tactile sensors to a curved surface according to the first embodiment of the present invention. FIG. 6 is a partial sectional view of the structure for attaching tactile sensors to a curved surface according to the first embodiment of the present invention. FIG. 7 is a plan view of FIG. 5. FIG. 8 is a side view of the structure for attaching tactile sensors to a curved surface according to the first embodiment of the present invention. The tactile sensor according to the first embodiment of the present invention is described in detail below with reference to FIGS. 5 to 8.

The tactile sensor unit 100 detects external force Fin or pressure when the external force or pressure is applied. The tactile sensor unit 100 may be configured to detect the external force Fin by using one of a contact resistance method, a capacitive method, a piezoelectric material method, and a pressure resistance method. For example, each of the tactile sensor units 100 may include a first sensor layer 110 and a second sensor layer 120 in order to implement the contact resistance method.

The first sensor layer 110 chiefly includes first sensing units 111, first signal lines 112, and fixing grooves 113.

The first sensing units 111, together with second sensing units 121, detect the external force Fin and generate detection signals. Each of the first sensing units 111 may be formed to have a regular quadrilateral as shown, but is not limited thereto. For example, the first sensing unit 111 may have any shape suitable for detecting a tactile sensation, such as a circle or a polygon. The first sensing units 111 are arranged in a matrix form as shown in FIG. 5, and the first sensing units 111 adjacent to each other are connected in a line.

The first signal lines 112 transfer the detection signals outputted from the first sensing units 111. The first signal lines 112 may be wired in a line along the first sensing units 111 connected together in a line, as shown in FIG. 5. Furthermore, the ends of the first signal lines 112 may be formed to be bent at a right angle and then to be gathered as shown FIG. 5. The first sensor layer 110 is formed on a flexible PCB (FPCB), and the first sensor layer 110 has flexibility to the extent that it may also be attached to a curved surface. Here, a space between the first signal lines 112 wired in a line is punched as shown, thereby improving flexibility.

Each of the fixing grooves 113 is a straight-line groove formed at the edge of the tactile sensor unit 100 which is not inserted into a sensor insertion groove 210 to be described later. The fixing grooves 113 are provided in order to fix the edge portion of the inserted tactile sensor unit 100 to one side of the sensor fixing unit 200 to be described later so that the inserted tactile sensor unit 100 dos not become unfastened. The fixing groove 113 may be formed to have a straight-line groove as shown or may be formed to have a circular hole. The shape and position of the fixing groove 113, although not shown, may be modified depending on the shape of a sensor fixing protrusion formed on one side of the sensor fixing unit 200. For reason of a design, the fixing grooves 113 may not be formed in the tactile sensor unit 100, but may be bonded to one side of the sensor fixing unit 200.

The second sensor layer 120 chiefly includes the second sensing units 121 and second signal lines 122. The second sensing units 121 have the same function and construction as the first sensing units 111. The second signal lines 122 have the same function as the first signal lines 112. The ends of the second signal lines 122, as shown in FIG. 5, are gathered at a central edge and then extended. Furthermore, although not shown, the fixing grooves 113 may not be formed in the first sensor layer 110, but may be formed at the edges of the second sensor layer 120 or may be formed both in the first sensor layer 110 and the second sensor layer 120.

The tactile sensor unit 100 is configured by stacking the first sensor layer 110 and the second sensor layer 120 so that they cross each other. More specifically, the first sensing units 111 and the second sensing units 121 are stacked so that they correspond to each other. Furthermore, the first sensor layer 110 and the second sensor layer 120 are orthogonal to each other, thus generally forming a lattice form. The tactile sensor unit 100 can be easily inserted into the curved surface of the sensor fixing unit 200 to be described later because the tactile sensor unit 100 forms a lattice form and thus has improved flexibility. Furthermore, the first sensing units 111 and the second sensing units 121 may be arranged in a matrix form in order to detect a position to which the external force Fin or pressure is applied.

The load bumpers 130 are provided so that repulsive force in response to the external force Fin is concentrated on the first sensing units 111 and the second sensing units 121, thereby improving the sensitivity of the tactile sensor unit 100. Each of the load bumpers 130 may be formed to have a circle having a specific height as shown in FIG. 5. The plane shape of the load bumper 130 is not limited to the circle, but may have any shape for concentrating repulsive force, such as a regular quadrilateral or a regular polygon. Furthermore, the load bumper 130 is made of material stiffer than the tactile sensor unit 100. It is preferred that the load bumper 130 have a smaller diameter than each of the first sensing unit 111 and the second sensing unit 121.

The temperature sensor units 140 are provided to measure temperature of an object to which the external force Fin is applied. As shown, the temperature sensor units 140 may be formed to have the same line form in which the second sensing units 121 are connected together in a line. Furthermore, as shown, the temperature sensor units 140 may correspond to the second sensing units 121 connected together in a line so that the plurality of temperature sensor units 140 is arranged in a row.

The sensor fixing unit 200 has one surface concavely curved and includes a plurality of the sensor insertion grooves 210 formed in the concave curved surface in order to attach the tactile sensor unit 100. The concave curved surface may be formed to be part of a sphere or part of a cylindrical surface. The external force Fin is supplied to the other surface of the sensor fixing unit 200, and the other surface of the sensor fixing unit 200 may be a convex curved surface. It is preferred that the sensor fixing unit 200 have the same thickness between the one surface, corresponding to an area to which the external force Fin is applied, and the other surface.

The sensor fixing unit 200 may further include sensor insertion grooves 210, grooves/protrusions, and sensor fixing protrusions.

The sensor insertion grooves 210 are formed in the concave curved surface of the sensor fixing unit 200. The sensor insertion grooves 210 may be straight-line grooves which are orthogonal to each other and formed in a matrix form. Furthermore, a point at which the straight-line groove horizontally formed crosses the straight-line groove vertically formed may be formed to have a regular quadrilateral depending on the size of the first sensing units 111 and the second sensing unit 121 as shown. Only the straight-line grooves may be formed in parts adjacent to the edge of the sensor fixing unit 200 as shown in FIGS. 5 and 7. Unlike in FIGS. 5 and 7, grooves of a lattice form may be formed up to the edge of the sensor fixing unit 200. An interval between the sensor insertion grooves 210 and the thickness of the sensor insertion grooves 210 are determined so that the relevant parts of the tactile sensor unit 100 are inserted into the sensor insertion grooves 210. Furthermore, the interval between the sensor insertion grooves 210 may be irregular depending on the curvature of the concave curved surface. It is preferred that the depth of the sensor insertion grooves 210 be greater than the thickness of the tactile sensor unit 100.

The grooves/protrusions may be further formed at the edge of one surface of or in the other surface of the sensor fixing unit 200. The grooves and protrusions are provided so that the sensor fixing unit 200 to be described later is coupled with the locking unit 500 to be described later. For example, a plurality of protrusions 220 may be formed along the edge of the convex curved surface of the sensor fixing unit 200. as shown in FIG. 8.

The sensor fixing unit 200 may be formed to have a shape that forms the tip of a finger of a robot, for example. That is, the sensor fixing unit 200 may be formed to have a specific thickness in a form in which a hemisphere and a hemi-cylinder are coupled so that the tactile sensor unit 100 is placed according to a part where the fingerprint of a person's finger is formed. Here, the sensor insertion grooves 210 are formed in the internal surface of the hemisphere or the hemi-cylinder. In addition, the sensor fixing unit 200 including the curved surface to which the tactile sensors are attached may be formed to have various curved surface forms depending on its purposes.

The sensor fixing unit 200 is formed by injecting flexible material, such as resilient synthetic resin such as polyurethane, silicon, latex, or PDMS, into a mold. That is, the sensor fixing unit 200 may be integrally injected through a mold in which the curved surface is formed.

Each of the sealing units 300 is provided to seal the sensor insertion grooves 210 formed in the sensor fixing unit 200. More specifically, the sealing unit 300 seals the sensor insertion groove 210 into which all the temperature sensor unit 140, the load bumper 130, and the tactile sensor unit 100 are inserted. As shown, the sealing unit 300 has a lattice form having the same curvature as that of the curved surface of the sensor insertion grooves 210. The sealing unit 300 may have any shape for sealing the sensor insertion grooves 210. For example, unlike in shown, the sensor insertion grooves 210 may have a curved surface which has the same curvature as that of the curved surface of the sensor fixing unit 200, but does not have grooves. Furthermore, it is preferred that the depth of the sensor insertion grooves 210 be determined to be 0.5 times to 3 times the thickness of the sealing unit 300. If the depth of the sensor insertion groove 210 is 0.5 times smaller than the thickness of the sealing unit 300, it is difficult to accurately detect a tactile sensation owing to an unstable structure. Furthermore, if the depth of the sensor insertion groove 210 is 3 times greater than the thickness of the sealing unit 300, the tactile sensor unit 100 may get out of order because an alien substance is infiltrated into the sensor insertion groove 210 in a manufacturing process.

The sealing unit 300 may be made of the same material as the sensor fixing unit 200 and may be integrally formed by performing injection into a mold.

The support unit 400 functions as a frame to support the sensor fixing unit 200. More specifically, the support unit 400 is formed to have a shape corresponding to the concave curved surface of the sensor fixing unit 200. For example, the support unit 400 may have a form in which a hemi-cylinder and a hemisphere are coupled. The support unit 400 may be made of metal material or hardening plastic material. Furthermore, the support unit 400 may be integrally formed by performing injection into a mold.

The locking unit 500 connects the sensor fixing unit 200 and the support unit 400 and fixes the edge of the tactile sensor unit 100. The locking unit 500 may include a side having a form to surround the edge of the sensor fixing unit 200 (e.g., the side curved and formed in an arch shape) and a rear face extended at a right angle to the side and then finished. Here, locking protrusions/locking grooves 510 formed to be coupled with the grooves/protrusions of the sensor fixing unit 200 may be further included in the side. More specifically, as shown in FIG. 8, a plurality of the grooves 510 may be formed at relevant parts so that the grooves 510 are coupled with the protrusions 220 of the sensor fixing unit 200. As described above, the locking unit 500 may be modified in any form if the form can couple the sensor fixing unit 200 and the support unit 400 which are modified depending on characteristic of an apparatus in which the tactile sensor is used. The locking unit 500 may be made of metal material or hardening plastic material. Furthermore, the locking unit 500 may be integrally formed by performing injection into a mold.

The load bumpers 130 or the temperature sensor units 140 may be omitted depending on selection in a design.

A method of attaching tactile sensors to a curved surface having the above construction according to the first embodiment of the present invention is described later.

Construction of Second Embodiment

A structure for attaching tactile sensors to a curved surface according to a second embodiment of the present invention chiefly includes tactile sensor units 100, load bumpers 130, temperature sensor units 140, a sensor fixing unit 200, sealing units 300, a support unit 400, and a locking unit 500.

Figure 9:
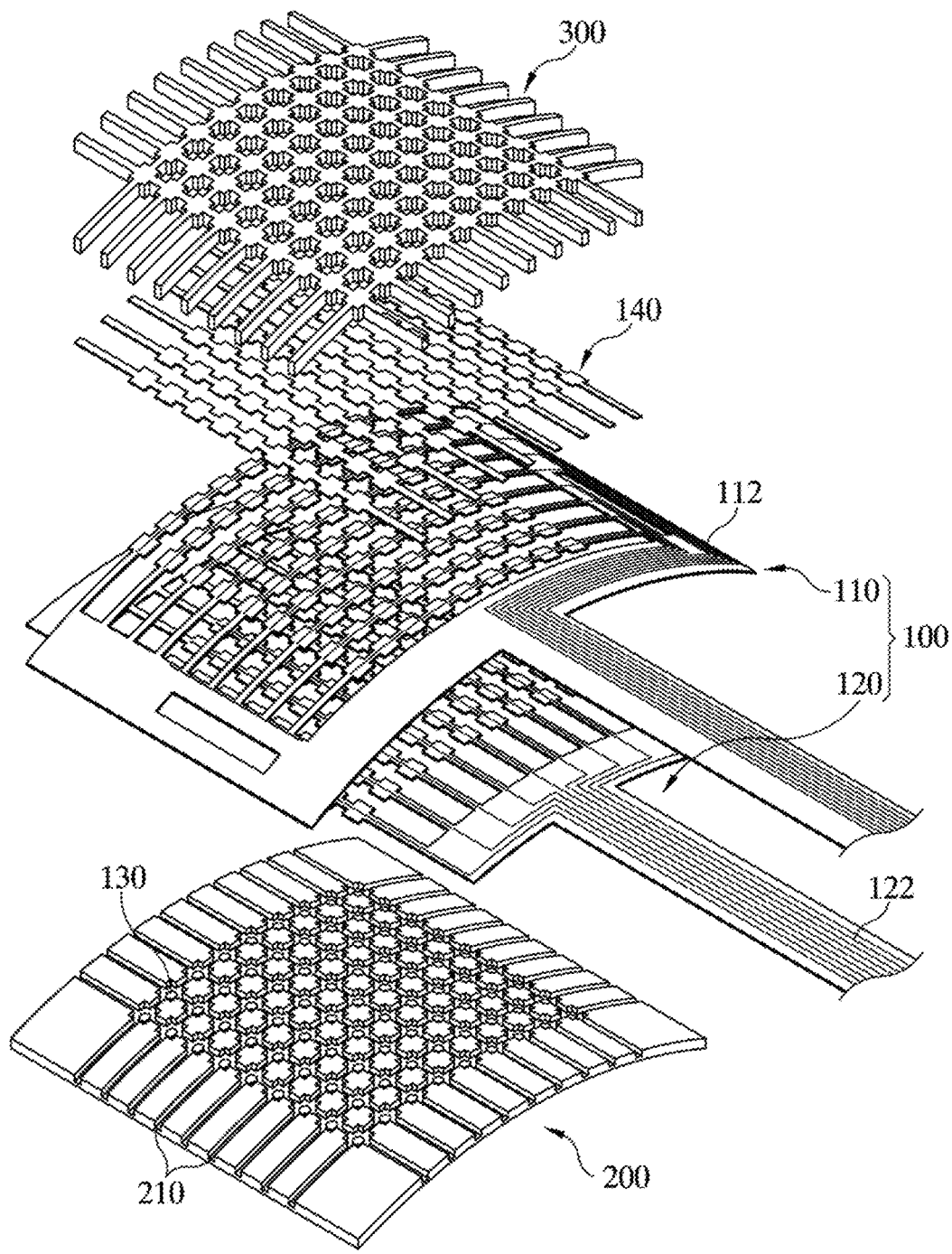
FIG. 9 is an exploded perspective view of a tactile sensor unit to a sealing unit, from among elements forming a structure for attaching tactile sensors to a curved surface according to a second embodiment of the present invention.
Figure 10:
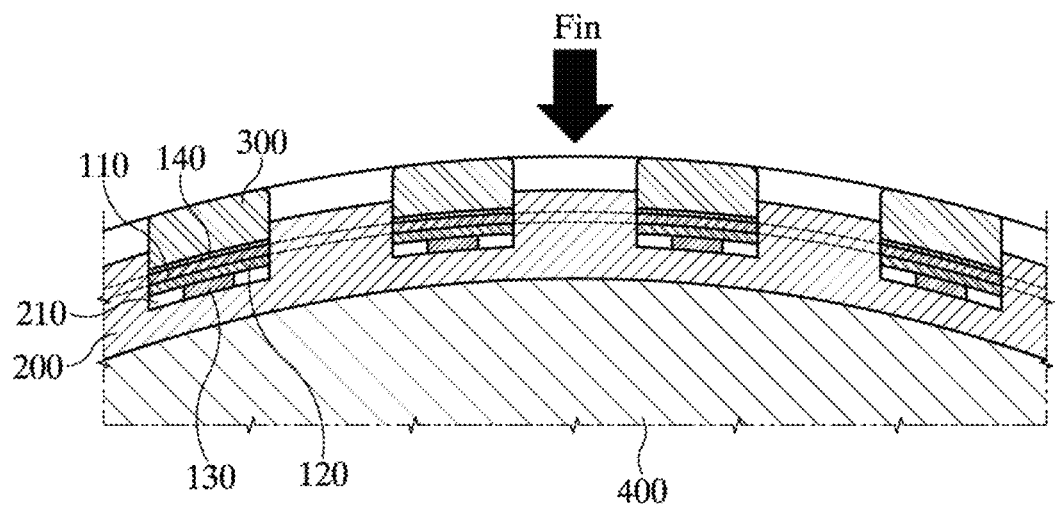
FIG. 10 is a partial sectional view of the structure for attaching tactile sensors to a curved surface according to the second embodiment of the present invention.
Figure 11:
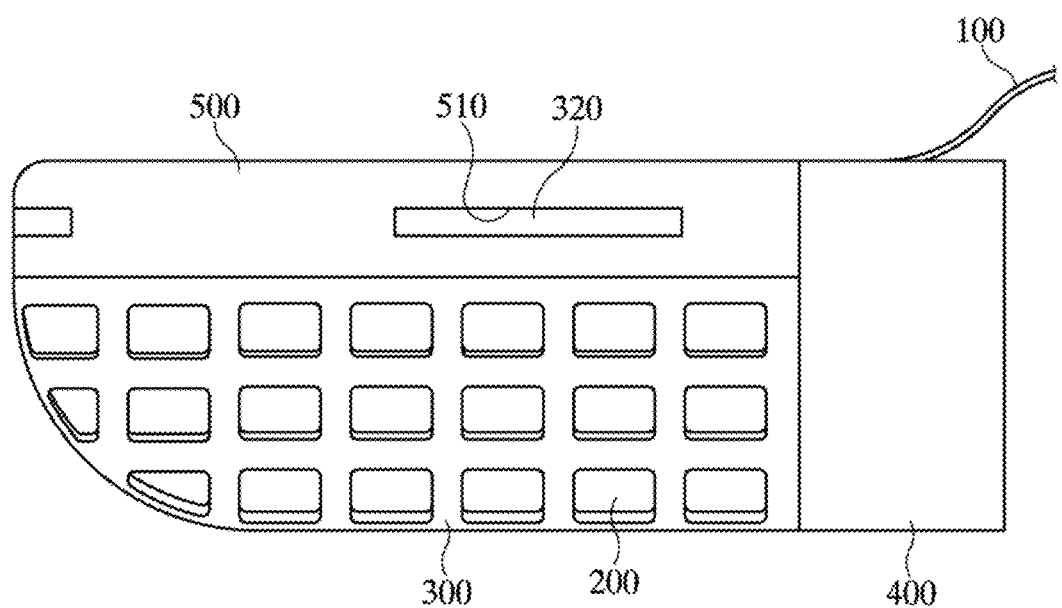
FIG. 11 is a side view of the structure for attaching tactile sensors to a curved surface according to the second embodiment of the present invention.

FIG. 9 is an exploded perspective view of the tactile sensor unit to the sealing unit, from among the elements forming the structure for attaching tactile sensors to a curved surface according to the second embodiment of the present invention. FIG. 10 is a partial sectional view of the structure for attaching tactile sensors to a curved surface according to the second embodiment of the present invention. FIG. 11 is a side view of the structure for attaching tactile sensors to a curved surface according to the second embodiment of the present invention. The structure for attaching tactile sensors to a curved surface according to the second embodiment of the present invention is described in detail below with reference to FIGS. 9 to 11.

The tactile sensor unit 100, the load bumpers 130, the temperature sensor units 140, the support unit 400, and the locking unit 500 have the same construction as those of the structure for attaching tactile sensors to a curved surface according to the first embodiment. In the present embodiment, locking protrusions/locking grooves formed in the locking unit 500 are provided to be coupled with the grooves/protrusions of the sealing units 300 to be described later. For example, a plurality of locking grooves 510 formed in the locking unit 500 is formed at parts corresponding to protrusions 320 formed in the sealing unit 300.

The sensor fixing unit 200 has one surface convexly formed in order to attach the tactile sensor unit 100 to the one surface, and a plurality of sensor insertion grooves 210 is formed in the concave curved surface. The convex curved surface may be formed to be part of a sphere and may be formed to be part of a cylindrical surface. Furthermore, external force Fin may be applied to the convex curved surface of the sensor fixing unit 200, as shown in FIG. 10. It is preferred that the sensor fixing unit 200 have the same thickness between the one surface, corresponding to an area to which the external force Fin is applied, and the other surface.

The plurality of sensor insertion grooves 210 is formed in the convex curved surface of the sensor fixing unit 200. The sensor insertion grooves 210 may include a plurality of straight-line grooves which are formed to be orthogonal to each other and formed in a lattice form. Furthermore, a point at which the straight-line groove horizontally formed crosses the straight-line groove vertically formed may be formed to have a regular quadrilateral depending on the size of the first sensing units 111 and the second sensing unit 121 as shown. An interval between the sensor insertion grooves 210 and the thickness of the sensor insertion grooves 210 are determined so that the relevant parts of the tactile sensor unit 100 are inserted into the sensor insertion grooves 210. Furthermore, the interval between the sensor insertion grooves 210 may be irregular depending on the curvature of the concave curved surface. It is preferred that the depth of the sensor insertion grooves 210 be greater than the thickness of the tactile sensor unit 100.

The sensor fixing unit 200 may be formed to have a shape that forms the tip of a finger of a robot, for example. That is, the sensor fixing unit 200 may be formed to have a specific thickness in a form in which a hemisphere and a hemi-cylinder are coupled so that the tactile sensor unit 100 is placed according to a part where the fingerprint of a person's finger is formed. Here, the sensor insertion grooves 210 are formed in the external surface of the hemisphere or the hemi-cylinder. In addition, the sensor fixing unit 200 including the curved surface to which the tactile sensors are attached may be formed to have various curved surface forms depending on its purposes.

The sealing unit 300 further include grooves/protrusions formed on one side or the other side of the sealing unit 300 formed as in the first embodiment. The grooves/protrusions are provided so that the sealing unit 300 is coupled with the locking unit 500. For example, as shown in FIG. 11, a plurality of the protrusion 320 is formed at the edge of the convex curved surface of the sealing unit 300.

The load bumpers 130 or the temperature sensor units 140 may be omitted depending on selection in a design.

Figure 12:
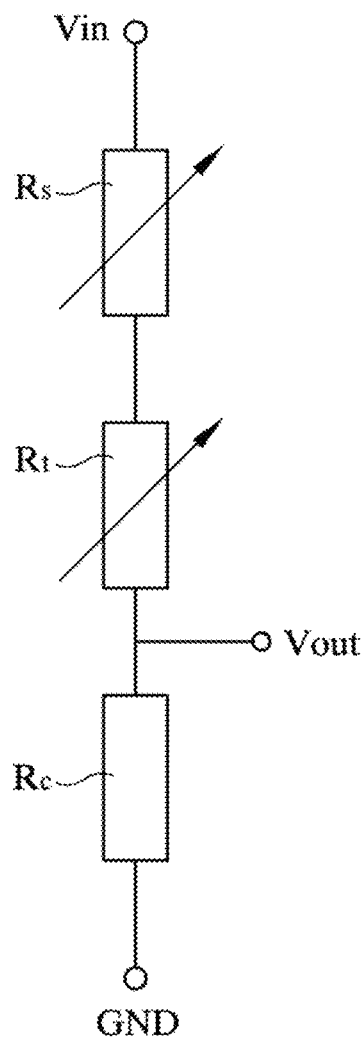
FIG. 12 is a circuit diagram of temperature compensation means having a PTC characteristic which is applicable to the present invention.

A construction capable of measuring external force more precisely through temperature compensation when the tactile sensor unit 100 according to the first embodiment and the second embodiment of the present invention uses a contact resistance method is described below. FIG. 12 is a circuit diagram of temperature compensation means having a Positive Temperature Coefficient (PTC) characteristic which is applicable to the present invention. As shown in FIG. 12, the resistor Rs of a contact resistance sensor, a feedback resistor Rc, and a temperature compensation resistor Rt having a PTC characteristic are coupled in series. Furthermore, an output voltage Vout is outputted from between the feedback resistor Rc and the temperature compensation resistor Rt having a PTC characteristic.

If temperature rises owing to the outside air, the tactile sensor of a contact resistance method has low resistance as compared to normal temperature under specific force. In the circuit diagram of temperature compensation means, such as that shown in FIG. 12, if the temperature compensation resistor Rt having a PTC characteristic is coupled in series to the resistor Rs and the feedback resistor Rc, pieces of resistance against temperature are offset, so that temperature is automatically compensated. For reference, the PTC characteristic refers to a characteristic in which resistance is increased when temperature rises. Consequently, external force or pressure can always be measured precisely without a change of sensitivity or malfunction of the tactile sensor according to a change of temperature.

Figure 13:
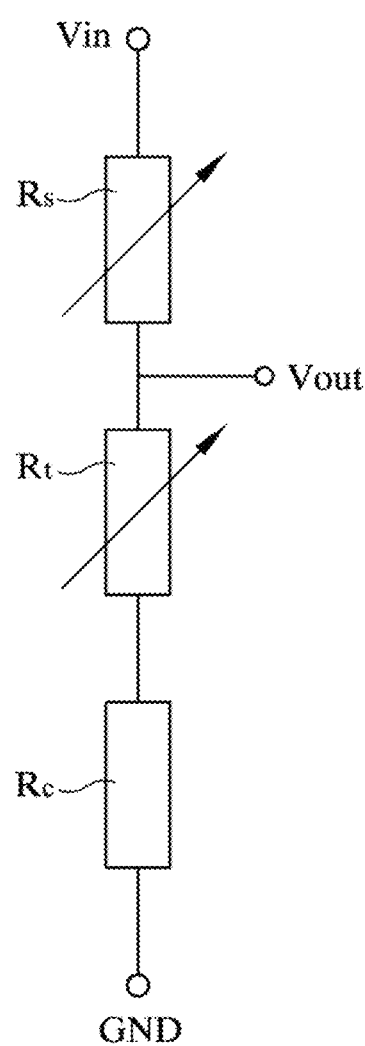
FIG. 13 is a circuit diagram of temperature compensation means having an NTC characteristic which is applicable to the present invention.

FIG. 13 is a circuit diagram of temperature compensation means having a Negative Temperature Coefficient (NTC) characteristic which is applicable to the present invention. As shown in FIG. 13, the resistor Rs of the contact resistance sensor, a feedback resistor Rc, and a temperature compensation resistor Rt having an NTC characteristic are coupled in series. Furthermore, an output voltage Vout is outputted from between the resistor Rs and the temperature compensation resistor Rt having an NTC characteristic.

If temperature rises owing to the outside air, the tactile sensor of a contact resistance method has low resistance as compared to normal temperature under specific force. In the circuit diagram of temperature compensation means, such as that shown in FIG. 13, if the temperature compensation resistor Rt having an NTC characteristic is coupled in series to the feedback resistor Rc in a potential difference circuit, pieces of resistance against temperature are offset, so that temperature is automatically compensated. For reference, the NTC characteristic refers to a characteristic in which resistance is decreased when temperature rises. Consequently, external force or pressure can always be measured precisely without a change of sensitivity or a malfunction of the tactile sensor according to a change of temperature.

A method of attaching tactile sensors to a curved surface having the above construction according to the second embodiment of the present invention is described later.

Manufacturing Method of First Embodiment

Figure 14:
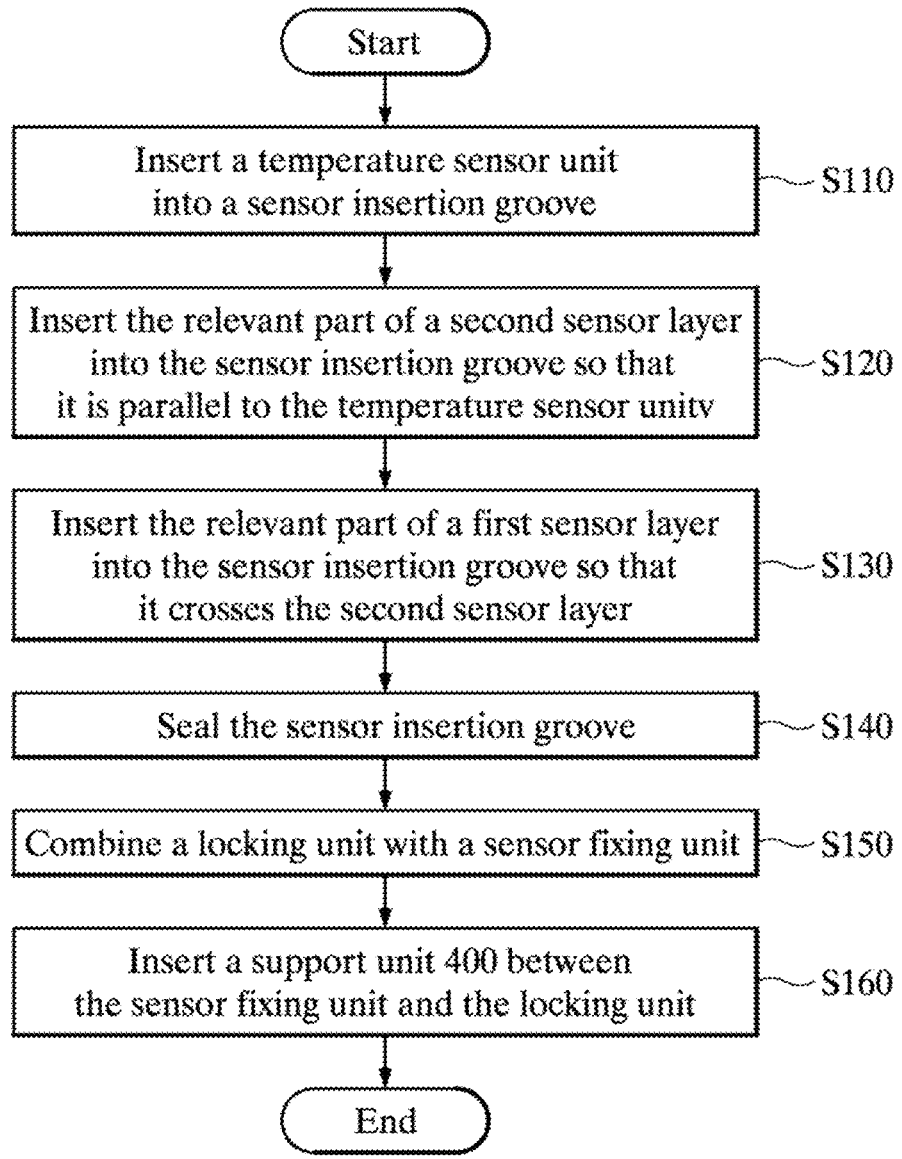
FIG. 14 is a flowchart illustrating a method of attaching tactile sensors to a curved surface according to a first embodiment of the present invention.

FIG. 14 is a flowchart illustrating a method of attaching tactile sensors to a curved surface according to a first embodiment of the present invention. The method of attaching tactile sensors to a curved surface according to the first embodiment of the present invention is described in detail below with reference to FIGS. 5 to 8 and 14.

The method of attaching tactile sensors to a curved surface according to the first embodiment of the present invention chiefly includes a temperature sensor unit insertion step (S110), a tactile sensor unit insertion step, a sealing step (S140), a locking unit coupling step (S150), and a support unit insertion step (S160).

First, in the temperature sensor unit insertion step (S110), the temperature sensor units 140 are inserted into the respective sensor insertion grooves 210 of the sensor fixing unit 200 in a row.

Next, the tactile sensor unit insertion step includes a second sensor layer insertion step (S120) and a first sensor layer insertion step (S130). First, in the second sensor layer insertion step (S120), the second sensor layer 120 is inserted into the sensor insertion groove 210 in parallel to the temperature sensor unit 140, as shown in FIG. 5. Here, the second sensing units 121 are inserted into the crossings of the sensor insertion groove 210. Furthermore, the load bumper 130 stacked on the second sensing unit 121 is inserted so that it is directed toward the sensor insertion groove 210. Next, in the first sensor layer insertion step (S130), the first sensor layer 110 is placed to cross the second sensor layer 120 and is then inserted into the sensor insertion groove 210. Here, the first sensing units 111 are inserted into the crossings of the sensor insertion grooves 210.

In the tactile sensor unit insertion step, however, unlike in FIG. 14, the first sensor layer 110 and the second sensor layer 120 may be first coupled to form the tactile sensor unit 100 so that they cross each other and may be then integrally inserted into the sensor insertion groove 210. In this case, it is preferred that the tactile sensor unit 100 be inserted into the sensor insertion groove 210 so that the temperature sensor units 140 and the second sensor layer 120 are parallel to each other.

Furthermore, the sensor fixing protrusions (not shown) formed in the sensor fixing unit 200 are coupled with the fixing grooves 113 formed in the tactile sensor unit 100. If the sensor fixing protrusions and the fixing grooves 113 do not exist for reasons of a design, the edges of the tactile sensor unit 100 may be bonded to the sensor fixing unit 200 by using epoxy or an instant adhesive.

Next, in the sealing step (S140), the sensor insertion groove 210 is sealed by the sealing unit 300. More specifically, as descried above, the sealing unit 300 is closely adhered to and inserted and sealed into the sensor insertion grooves 210 sequentially including the temperature sensor unit 140, the load bumper 130, and the tactile sensor unit 100.

Here, a face where the sensor fixing unit 200 comes in contact with the sealing unit 300 may be bonded and fixed using an adhesive. Here, epoxy or an instant adhesive may be used as the adhesive.

Next, in the locking unit coupling step (S150), the side of the locking unit 500 is inserted into the side of the sensor fixing unit 200. For example, the locking grooves 510 of the locking unit 500 may be inserted into and coupled with a protrusion 220 formed in the outer edge of the sensor fixing unit 200. Here, the locking unit 500 is inserted so that the concave curved surface of the sensor fixing unit 200 faces the rear face of the locking unit 500. Furthermore, the ends of the first signal lines 112 and the second signal lines 122 not inserted into the sensor insertion groove 210 may be externally drawn out as shown in FIG. 8. If the protrusion 220 is not formed in the sensor fixing unit 200 for reasons of a design, a face where the locking unit 500 comes in contact with the sensor fixing unit 200 may be bonded and combined. Epoxy or an instant adhesive may be used as an adhesive for bonding the face where the locking unit 500 comes in contact with the sensor fixing unit 200.

Finally, in the support unit coupling step (S160), the support unit 400 is inserted into an empty space between the sensor fixing unit 200 and the locking unit 500. Here, since the support unit 400 and the locking unit 500 are closely adhered to each other, the first signal lines 112 and the second signal lines 122 provided between the support unit 400 and the locking unit 500 are stably fixed.

Manufacturing Method of Second Embodiment

Figure 15:
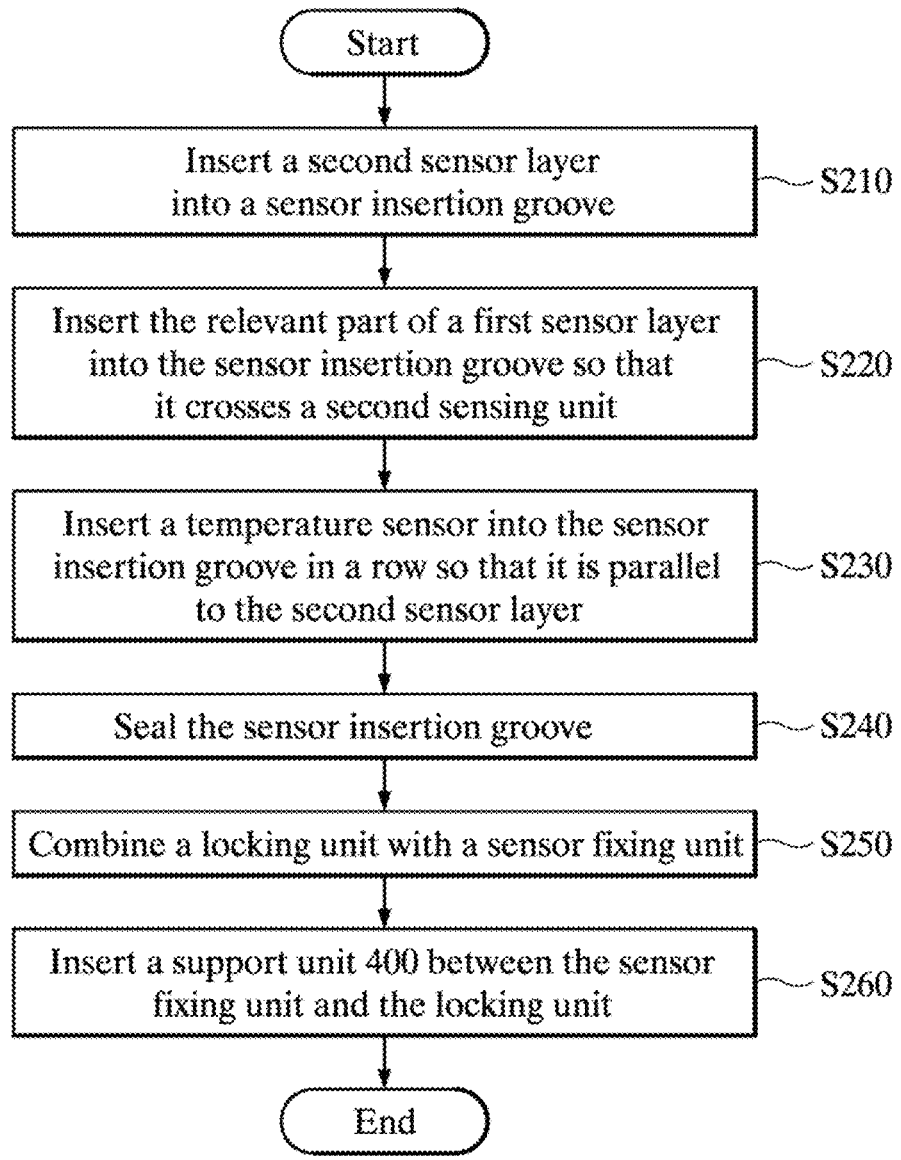
FIG. 15 is a flowchart illustrating a method of attaching tactile sensors to a curved surface according to a second embodiment of the present invention.

FIG. 15 is a flowchart illustrating a method of attaching tactile sensors to a curved surface according to a second embodiment of the present invention. The method of attaching tactile sensors to a curved surface according to the second embodiment of the present invention is described in detail below with reference to FIGS. 9 to 11 and 15.

The method of attaching tactile sensors to a curved surface according to the second embodiment of the present invention chiefly includes a tactile sensor unit insertion step, a temperature sensor unit insertion step (S230), a sealing step (S240), a locking unit coupling step (S250), and a support unit insertion step (S260).

The tactile sensor unit insertion step includes a second sensor layer insertion step (S210) and a first sensor layer insertion step (S220). First, in the second sensor layer insertion step (S210), the second sensor layer 120 is inserted into the sensor insertion groove 210. Here, the second sensing units 121 are inserted into the crossings of the sensor insertion grooves 210. Furthermore, the load bumper 130 stacked on the second sensing units 121 is inserted so that they are directed toward the sensor insertion grooves 210. Next, in the first sensor layer insertion step (S220), the first sensor layer 110 is placed to cross the second sensor layer 120 and is then inserted into the sensor insertion groove 210. Here, the first sensing units 111 are inserted into the crossings of the sensor insertion grooves 210.

Unlike in FIG. 15, in the tactile sensor unit insertion step, the first sensor layer 110 and the second sensor layer 120 may be first coupled to form the tactile sensor unit 100 so that they cross each other and may be then integrally inserted into the sensor insertion groove 210.

Furthermore, the sensor fixing protrusions (not shown) formed in the sensor fixing unit 200 are coupled with the fixing grooves 113 formed in the tactile sensor unit 100. If the sensor fixing protrusions and the fixing grooves 113 do not exist for reasons of a design, the edges of the tactile sensor unit 100 may be bonded to the sensor fixing unit 200 by using epoxy or an instant adhesive.

Next, in the temperature sensor insertion step (S230), the temperature sensor unit 140 is inserted into the sensor insertion groove 210 in a row so that it is parallel to the second sensor layer 120.

The sealing step (S240) is the same as the relevant step of the method of attaching tactile sensors to a curved surface according to the first embodiment, and a description thereof is omitted.

In the locking unit coupling step (S250), the side of the locking unit 500 is inserted into the side of the sensor fixing unit 200 or the sealing units 300 and coupled thereto. For example, the locking grooves 510 of the locking unit 500 are inserted into the protrusion 320 formed in the lateral edge of the sealing unit 300 and then coupled thereto. Here, the locking unit 500 is inserted so that the concave curved surface of the sensor fixing unit 200 faces the rear face of the locking unit 500. Furthermore, the ends of the first signal lines 112 and the second signal lines 122 not inserted into the sensor insertion groove 210 may be externally drawn out, as shown in FIG. 11. If the protrusions 320 are not formed in the sealing unit 300 for reasons of a design, a face where the locking unit 500 comes in contact with the sensor fixing unit 200 or a face where the locking unit 500 comes in contact with the sealing unit 300 may be bonded using an adhesive. Here, epoxy or an instant adhesive may be used as the adhesive.

The support unit insertion step (S260) is the same as the relevant step of the method of attaching tactile sensors to a curved surface according to the first embodiment, and a description thereof is omitted.

In accordance with the present invention, the sensor insertion grooves are formed in a matrix form in the curved surface to which the tactile sensor units are attached, and the tactile sensor units are formed in a matrix form and are inserted into the respective sensor insertion grooves. Accordingly, there is an advantage in that the tactile sensor units can be easily attached.

Furthermore, in accordance with the first embodiment of the present invention, a face in which the sensor insertion grooves of the sensor attachment units are formed is concavely curved. Accordingly, there is an advantage in that durability is improved because the tactile sensor unit is not peeled off or broken.

Furthermore, in accordance with the present invention, the sensor attachment unit and the sealing unit can be subject to mass production because they are injected into a mold, and the tactile sensors attached to the curved surface can be subject to mass production because the tactile sensor unit, the sensor attachment unit, and the sealing unit are mechanically assembled. Accordingly, there are advantages in that productivity and economy are improved.

As described above, a person having ordinary skill in the art to which the present invention pertains will understand that the present invention may be implemented in various detailed forms without changing the technical spirit or indispensable characteristics of the present invention. It will be understood that the above-described embodiments are illustrative and not limitative from all aspects. The scope of the present invention is defined by the appended claims rather than the detailed description, and the present invention should be construed to cover all modifications or variations induced from the meaning and scope of the appended claims and their equivalents.

What is claimed is:

1. A structure for attaching tactile sensors to a curved surface, comprising:
   a sensor fixing unit 200 configured to have at least part of one surface curved and to have a plurality of sensor insertion grooves 210, crossing each other, formed in the one surface in a matrix form;
   tactile sensor units 100 formed in a matrix form, inserted into the respective sensor insertion grooves 210, and configured to detect external force Fin;
   sealing units 300 configured to seal the sensor insertion grooves 210; and
   a support unit 400 configured to come in contact with one face of the sealing units 300 or the sensor fixing units 200 and to support the sensor fixing units 200.

2. The structure as claimed in claim 1, wherein the tactile sensor unit 100 detects the external force Fin by using any one of a contact resistance method, a capacitive method, a piezoelectric material method, and a pressure resistance method.

3. The structure as claimed in claim 1, wherein each of the tactile sensor units 100 comprises:
   a first sensor layer 110 configured to include a plurality of first sensing units 111 wired in one direction and inserted into respective crossings of the sensor insertion grooves 210; and
   a second sensor layer 120 configured to include a plurality of second sensing units 121, wired in one direction and inserted into respective crossings of the sensor insertion grooves 210, and stacked to cross the first sensor layer 110.

4. The structure as claimed in claim 1, further comprising load bumpers 130 provided between the tactile sensor unit 100 and the sensor fixing unit 200.

5. The structure as claimed in claim 1, further comprising a locking unit 500 coupled with one side of at least one of the sensor fixing unit 200 and the sealing unit 300 and configured to couple the sensor fixing unit 200 and the support unit 400.

6. The structure as claimed in claim 5, wherein:
   at least one of the sensor fixing unit 200 and the sealing unit 300 further comprises grooves/protrusions formed one side, and
   the locking unit 500 comprises locking protrusions/locking grooves coupled with the grooves/protrusions.

7. The structure as claimed in claim 5, wherein:
   the sensor fixing unit 200 comprises sensor fixing protrusions formed on one side, and
   fixing grooves 113 formed to be coupled with the sensor fixing protrusions are formed in respective parts into which the sensor insertion grooves 210 are not inserted, from the tactile sensor unit 100.

8. The structure as claimed in claim 5, wherein the locking unit 500 is combined with one side of at least one of the sensor fixing unit 200 and the sealing unit 300 by using bonding.

9. The structure as claimed in claim 1, wherein the tactile sensor unit 100 is combined with the sensor fixing unit 200 by using bonding.

10. The structure as claimed in claim 1, wherein the sensor fixing unit 200 has the one surface in which the sensor insertion grooves 210 are formed concavely curved.

11. The structure as claimed in claim 10, further comprising a temperature sensor unit 140 provided between the tactile sensor 100 and the sensor fixing unit 200 and configured to detect temperature.

12. The structure as claimed in claim 1, wherein the sensor fixing unit 200 has the one surface in which the sensor insertion grooves 210 are formed convexly curved.

13. The structure as claimed in claim 12, further comprising a temperature sensor unit 140 provided between the tactile sensor unit 100 and the sealing unit 300 and configured to detect temperature.

14. The structure as claimed in claim 1, wherein the sealing unit 300 is curved to have an identical curvature with the sensor fixing unit 200.

15. The structure as claimed in claim 1, wherein a depth of the sensor insertion groove 210 is 0.5 times to 3 times a thickness of the sealing unit 300.

16. The structure as claimed in claim 1, wherein at least one of the sensor fixing unit 200 and the sealing unit 300 comprises at least one of flexible polyurethane, PDMS, silicon, latex, and synthetic resin materials.

* * * * *